US009664612B2

(12) United States Patent
Mitchell et al.

(10) Patent No.: US 9,664,612 B2
(45) Date of Patent: May 30, 2017

(54) METHOD AND APPARATUS FOR GENERATING THREE-DIMENSIONAL IMAGE INFORMATION

(71) Applicant: Steropes Technologies, LLC, Pensacola, FL (US)

(72) Inventors: Thomas N. Mitchell, Bowen Island (CA); Ichiro Shinkoda, Vancouver (CA)

(73) Assignee: Steropes Technologies, LLC, Pensacola, FL (US)

( * ) Notice: Subject to any disclaimer, the term of this patent is extended or adjusted under 35 U.S.C. 154(b) by 548 days.

(21) Appl. No.: 13/724,819

(22) Filed: Dec. 21, 2012

(65) Prior Publication Data

US 2013/0176566 A1   Jul. 11, 2013

Related U.S. Application Data

(63) Continuation-in-part of application No. PCT/CA2010/000986, filed on Jun. 25, 2010, and a
(Continued)

(51) Int. Cl.
*G01J 4/00* (2006.01)
*G01N 21/21* (2006.01)
(Continued)

(52) U.S. Cl.
CPC ......... *G01N 21/21* (2013.01); *G02B 27/2264* (2013.01); *G02B 27/26* (2013.01);
(Continued)

(58) Field of Classification Search
CPC ............... G02B 27/2264; G03B 35/04; H04N 13/0217; H04N 13/0434; H04N 13/0438; G01N 21/21
See application file for complete search history.

(56) References Cited

U.S. PATENT DOCUMENTS 5,596,363 A * 1/1997 Christian ................. 348/58
5,742,333 A * 4/1998 Faris .................. 348/60
(Continued)

FOREIGN PATENT DOCUMENTS

CN   1489446   4/2004
EP   0715198   5/1996
(Continued)

OTHER PUBLICATIONS

Chung, Hugh; International Search Report from corresponding PCT Application Serial No. PCT/CA2010/000986; search completed on Mar. 18, 2011.
(Continued)

*Primary Examiner* — Kara E Geisel
*Assistant Examiner* — Maurice Smith
(74) *Attorney, Agent, or Firm* — Kristofer E. Elbing

(57) ABSTRACT

A method and apparatus for generating three-dimensional image information is disclosed. The apparatus includes a lens having a single imaging path operable to direct light captured within a field of view of the lens to an aperture plane of the lens. The apparatus also includes a polarizer located proximate the aperture plane, the polarizer including a first portion disposed to transmit light having a first polarization state through a first portion of the single imaging path and a second portion disposed to transmit light having a second polarization state through a second portion of the single imaging path, the first and second portions of the single imaging path providing respective first and second perspective viewpoints within the field of view of the lens. The apparatus further includes a modulator disposed in the single imaging path, the modulator being operable to selectively change a polarization state of light passing through the modulator to alternate between forming a first image through the first portion of the single imaging path and
(Continued)

forming a second image through the second portion of the single imaging path, the first image representing objects within the field of view from the first perspective viewpoint and the second image representing the objects from the second perspective viewpoint, the first and second images together being operable to represent three dimensional spatial attributes of the objects.

16 Claims, 8 Drawing Sheets

Related U.S. Application Data continuation of application No. PCT/CA2011/000739, filed on Jun. 21, 2011.

(51) Int. Cl.
- H04N 13/04 (2006.01)
- G02B 27/22 (2006.01)
- G02B 27/26 (2006.01)
- G03B 35/04 (2006.01)
- G03B 35/26 (2006.01)
- H04N 13/02 (2006.01)

(52) U.S. Cl.
CPC ............ *G03B 35/04* (2013.01); *G03B 35/26* (2013.01); *H04N 13/0217* (2013.01); *H04N 13/0434* (2013.01); *H04N 13/0438* (2013.01)

(56) References Cited

U.S. PATENT DOCUMENTS

| | | | |
|---|---|---|---|
| 5,828,487 A | | 10/1998 | Greening et al. |
| 5,964,696 A | * | 10/1999 | Mihalca et al. ............... 600/166 |
| 6,002,518 A | * | 12/1999 | Faris .............................. 359/465 |
| 6,275,335 B1 | | 8/2001 | Costales |
| 6,400,394 B1 | | 6/2002 | Kim et al. |
| 6,512,892 B1 | * | 1/2003 | Montgomery et al. ....... 396/326 |
| 7,324,279 B2 | | 1/2008 | Penn |
| 2005/0285946 A1 | * | 12/2005 | Raynor .................... 348/207.99 |
| 2006/0221444 A1 | * | 10/2006 | Fukaishi ............ G02B 27/2214 359/472 |
| 2007/0002132 A1 | * | 1/2007 | Kim et al. ....................... 348/57 |
| 2007/0051890 A1 | * | 3/2007 | Pittman ........................ 250/332 |
| 2007/0132953 A1 | | 6/2007 | Silverstein |
| 2009/0079900 A1 | * | 3/2009 | Ohta et al. ..................... 349/58 |
| 2010/0060721 A1 | | 3/2010 | Chen et al. |

FOREIGN PATENT DOCUMENTS

| | | | | |
|---|---|---|---|---|
| JP | 08152561 | | 6/1996 | |
| JP | 20035057 | | 2/2003 | |
| WO | 9801769 | | 4/1998 | |
| WO | WO 98/17169 | * | 4/1998 | ............... A61B 1/00 |
| WO | 0106282 | | 1/2001 | |
| WO | 0246827 | | 6/2002 | |
| WO | 2011003208 | | 1/2011 | |

OTHER PUBLICATIONS

Abou-Antoun, Patrick; International Search Report from corresponding PCT Application Serial No. PCT/CA2011/000739; search completed on Sep. 7, 2011.

* cited by examiner

METHOD AND APPARATUS FOR GENERATING THREE-DIMENSIONAL IMAGE INFORMATION

CROSS-REFERENCE TO RELATED APPLICATIONS

This application is a Continuation-in-Part of PCT International Application No. PCT/CA2010/000986 filed on Jun. 25, 2010 and a Continuation of PCT International Application No. PCT/CA2011/000739 filed on Jun. 21, 2011, which claims priority to PCT international Application No. PCT/CA2010/000986 filed on Jun. 25, 2010, the entire contents of which are incorporated herein by reference.

BACKGROUND OF THE INVENTION

1. Field of Invention

This invention relates generally to generating three-dimensional image information and more particularly to generating three-dimensional image information using a single imaging path.

2. Description of Related Art

In conventional two-dimensional (2D) imaging, rays of light representing objects in a three-dimensional (3D) scene are captured and mapped onto a 2D image plane, and thus depth information is not recorded. Stereoscopic optical systems are capable of producing images that represent depth information by producing separate images from differing perspective viewpoints. The separate images may be separately presented to respective left and right eyes of a user so as to mimic operation of the human eyes in viewing a real scene and allowing the user to perceive depth in the presented views. The separated or stereo images are generally produced by an optical system having either a pair of spatially separated imaging paths or by using different portions of a single imaging path to produce images having differing perspective viewpoints. The images may then be presented using eyewear that is able to selectively permit the separate images to reach the user's respective left and right eyes. Alternatively, a special display may be configured to project spatially separated images toward the user's respective left and right eyes.

The use of a stereoscopic imaging also finds application in the field of surgery where a 3D endoscope may be used to provide a 3D view to the surgeon. Stereoscopic imaging may also be useful in remote operations, such as undersea exploration for example, where control of a robotic actuator is facilitated by providing 3D image information to an operator who is located remotely from the actuator. Other applications of stereoscopic imaging may be found in physical measurement systems and in 3D film production equipment used in the entertainment industry.

SUMMARY OF THE INVENTION

In accordance with one aspect of the invention there is provided an apparatus for generating three-dimensional image information. The apparatus includes a lens having a single imaging path operable to direct light captured within a field of view of the lens to an aperture plane of the lens, and a polarizer located proximate the aperture plane, the polarizer including a first portion disposed to transmit light having a first polarization state through a first portion of the single imaging path and a second portion disposed to transmit light having a second polarization state through a second portion of the single imaging path, the first and second portions of the single imaging path providing respective first and second perspective viewpoints within the field of view of the lens. The apparatus also includes a modulator disposed in the single imaging path; the modulator being operable to selectively change a polarization state of light passing through the modulator to alternate between forming a first image through the first portion of the single imaging path and forming a second image through the second portion of the single imaging path, the first image representing objects within the field of view from the first perspective viewpoint and the second image representing the objects from the second perspective viewpoint, the first and second images together being operable to represent three dimensional spatial attributes of the objects.

A location of the aperture plane may be defined by one of a location of a physical aperture of the lens, or a location of a conjugate of the physical aperture.

The first portion of the polarizer may include a linear polarizer having a first linear polarization orientation and the second portion of the polarizer may include a linear polarizer having a second linear polarization orientation, the first linear polarization orientation being orthogonal to the second linear polarization orientation.

The first linear polarization orientation may be oriented at 45 degrees.

The modulator may be disposed in the single imaging path after the polarizer, and the modulator may be operably configured to alternate between transmitting light having the first linear polarization state and transmitting light having the second linear polarization state.

A quarter wave plate may be disposed in the single imaging path after the modulator.

The modulator may be disposed in the single imaging path before the polarizer, and the modulator is operably configured to select one of the first and second linear polarization states for transmission, and to alternate between transmitting the selected linear polarization state, and causing a 90° change in polarization orientation of the selected linear polarization state.

A quarter wave plate may be disposed in the single imaging path before the modulator.

The first portion of the polarizer may include a polarizer having a left-handed elliptical polarization orientation and the second portion of the polarizer may include a polarizer having a right-handed elliptical polarization orientation.

The modulator may be disposed in the single imaging path after the polarizer, and the modulator may be operably configured to alternate between transmitting light having the left-handed elliptical polarization orientation and transmitting light having the right-handed elliptical polarization orientation.

The modulator may be disposed in the single imaging path before the polarizer, and the modulator may be operably configured to select one of the left-handed and right-handed elliptical polarization orientations for transmission, and to alternate between transmitting the selected polarization orientation, and causing the selected polarization orientation to undergo a change between the left-handed polarization orientation and the right-handed polarization orientation.

The left-handed elliptical polarization orientation may include a left-handed circular polarization orientation and the right-handed elliptical polarization orientation may include a right-handed circular polarization orientation.

The modulator may be disposed in front of the lens.

The apparatus may include an image sensor, the image sensor being operably configured to separately record the first and second images.

The modulator may be disposed between the lens and the image sensor.

The modulator may include a liquid crystal material.

The modulator may include a Faraday rotator.

The modulator may include a spatial modulator operable to move to alternate between introducing a first region of the modulator having the first polarization orientation into the single imaging path, and introducing a second region of the modulator having the second polarization orientation into the single imaging path.

The modulator may be disposed at a location in the single imaging path at which a convergence or divergence angle of the captured light is less than an angle of acceptance criteria associated with the modulator.

The polarizer may include a polarizing coating applied to a surface of a lens element disposed proximate to the aperture plane.

A displacement between the polarizer and the aperture plane may be sufficiently small, such that intensity variations in the first and second images due to vignetting by the first and second portion of the polarizer may be below a threshold that is detectable by the human eye.

The displacement may be sufficiently small to reduce the intensity variations to below 30% across an image plane associated with the first and second images.

The lens may include a plurality of generally circular lens elements defining a generally circular cross-section single imaging path and the polarizer may include a left half and a right half, the respective left and right halves of the polarizer defining respective left and right semicircular portions of the single imaging path.

The lens may include a plurality of generally circular lens elements defining a generally circular cross-section single imaging path and the polarizer may include a left sector and a right sector, the respective left and right sectors of the polarizer defining respective left and right sectors of the single imaging path disposed about a vertical centerline of the lens.

The first and second portions of the polarizer may be operable to vary in extent to cause the first and second perspective viewpoints to change location while forming the first and second images, the change in perspective viewpoint location providing a corresponding change in the representation of the three dimensional spatial attributes.

The apparatus may include an actuator coupled to the polarizer, the actuator being operably configured to cause an orientation of the polarizer to be rotated by 90 degrees to facilitate selectively configuring the apparatus to generate images in one of a landscape orientation and a portrait orientation.

The apparatus may further comprise a first variable stop disposed in the first portion of the single imaging path proximate the polarizer and a second variable stop disposed in the second portion of the single imaging path proximate the polarizer.

The stops may be irises and may be disposed in front of the polarizer.

In accordance with another aspect of the invention there is provided a method for generating three-dimensional image information using a lens having a single imaging path and an associated field of view. The method involves directing light captured within the field of view of the lens to an aperture plane of the lens, and receiving the captured light at a polarizer located proximate the aperture plane, the polarizer including a first portion disposed to transmit light having a first polarization state through a first portion of the single imaging path and a second portion disposed to transmit light having a second polarization state through a second portion of the single imaging path, the first and second portions of the single imaging path providing respective first and second perspective viewpoints within the field of view of the lens. The method also involves controlling a modulator disposed in the single imaging path to selectively change a polarization state of light passing through the modulator to alternate between forming a first image through the first portion of the single imaging path and forming a second image through the second portion of the single imaging path, the first image representing objects within the field of view from the first perspective viewpoint and the second image representing the objects from the second perspective viewpoint, the first and second images together being operable to represent three dimensional spatial attributes of the objects.

Directing light to an aperture plane of the lens may involve directing light captured within the field of view of the lens to an aperture plane of the lens located at one of a location of a physical aperture of the lens, or a location of a conjugate of the physical aperture.

Receiving the captured light may involve receiving light having a first linear polarization orientation through the first portion of the polarizer and receiving light having a second linear polarization orientation through the second portion of the polarizer, the first linear polarization orientation being oriented orthogonal to the second linear polarization orientation.

The first linear polarization orientation may be oriented at 45 degrees.

The modulator may be disposed in the single imaging path after the polarizer, and controlling the polarization state of the modulator may involve alternating between transmitting light having the first linear polarization state and transmitting light having the second linear polarization state.

Linearly polarized light transmitted by the modulator may be directed through a quarter wave plate, thereby rendering light transmitted by the quarter wave plate circularly polarized.

The modulator may be disposed in the single imaging path before the polarizer, and controlling the polarization state of the modulator may involve selecting one of the first and second linear polarization states for transmission, and alternating between transmitting the selected linear polarization state and causing a 90° change in polarization orientation of the selected linear polarization state. Directing light to an aperture plane of the lens may involve directing light captured within the field of view of the lens through a quarter wave plate disposed in front of the modulator, thereby rendering linearly polarized at least one of circularly polarized light and elliptically polarized light from the objects.

Rendering linearly polarized may involve rendering polarized to one of the first polarized state and the second polarized state the one of the circularly polarized light and the elliptically polarized light.

Receiving the captured light may involve receiving light having a left-handed elliptical polarization state through the first portion of the polarizer and receiving light having a right-handed elliptical polarization state through the second portion of the polarizer.

The modulator may be disposed in the single imaging path after the polarizer, and controlling the polarization state of the modulator may involve alternating between transmitting light having the left-handed elliptical polarization state and transmitting light having the right-handed elliptical polarization state.

The modulator may be disposed in the single imaging path before the polarizer, and controlling the polarization state of the modulator may involve selecting one of the left-handed and right-handed elliptical polarization states for transmission, and alternating between transmitting the selected polarization state and causing the selected polarization state to undergo a change between the left-handed polarization state and the right-handed polarization state.

The left-handed elliptical polarization state may be a left-handed circular polarization state and the right-handed elliptical polarization state may be a right-handed circular polarization state.

Controlling the polarization state of the modulator may involve controlling a polarization state of a modulator disposed in front of the lens.

Controlling the polarization state of the modulator may involve controlling a state of a liquid crystal material.

Controlling the polarization state of the modulator may involve controlling a state of a Faraday rotator.

Controlling the polarization state of the modulator may involve moving the modulator to alternate between introducing a first region of the modulator having the first polarization state into the single imaging path, and introducing a second region of the modulator having the second polarization state into the single imaging path.

Controlling the polarization state of the modulator may involve controlling a polarization state of a modulator disposed at a location in the single imaging path at which a convergence or divergence angle of the captured light may be less than an angle of acceptance criteria associated with the modulator.

Receiving the captured light at the polarizer may involve receiving the captured light at a polarizing coating applied to a surface of a lens element disposed proximate to the aperture plane.

Receiving the captured light at the polarizer may involve receiving the captured light at a polarizer displaced from the aperture plane by a sufficiently small displacement such that intensity variations in the first and second images due to vignetting by the first and second portion of the polarizer may be below a threshold that may be detectable by the human eye.

The displacement may be sufficiently small to reduce the intensity variations to below 30% across an image plane associated with the first and second images.

The lens may include a plurality of generally circular lens elements defining a generally circular cross-section single imaging path and receiving the captured light may involve transmitting light having the first polarization state through a left half of the polarizer and transmitting the light having the second polarization state through a right half of the polarizer, the respective left and right halves of the polarizer defining respective left and right semicircular portions of the single imaging path.

The lens may include a plurality of generally circular lens elements defining a generally circular cross-section single imaging path and receiving the captured light may involve transmitting light having the first polarization state through a left sector portion of the polarizer and transmitting the light having the second polarization state through a right sector portion of the polarizer, the left and right sector portions being disposed about a vertical centerline of the lens.

The method may involve varying an extent of the first and second portions of the imaging path to cause the first and second perspective viewpoints to change location while forming the first and second images, the change in perspective viewpoint location providing a corresponding change in the representation of the three dimensional spatial attributes.

The method may involve selectively rotating the polarizer by 90 degrees to generate images in one of a landscape orientation and a portrait orientation.

Receiving the captured light through the polarizer may involve receiving captured light associated with the first portion of the single imaging path through a first variable stop and receiving captured light associated with the second portion of the single imaging path through a second variable stop.

The variable stops may be irises.

The captured light associated with the first portion of the single imaging path may be directed to the polarizer through the first variable stop and the captured light associated with the second portion of the single imaging path may be directed to the polarizer through the second variable stop.

The method may involve adjusting a depth of focus of the apparatus along the first portion of the imaging path by adjusting the first variable stop and adjusting a depth of focus of the apparatus along the second portion of the imaging path by adjusting the second variable stop.

In accordance with another aspect of the invention there is provided an apparatus for generating three-dimensional image information using a lens having a single imaging path and an associated field of view. The apparatus includes provisions for directing light captured within the field of view of the lens to an aperture plane of the lens, provisions for transmitting light having a first polarization state through a first portion of the single imaging path, and provisions for transmitting fight having a second polarization state through a second portion of the single imaging path, the first and second portions of the single imaging path providing respective first and second perspective viewpoints within the field of view of the lens. The apparatus also includes provisions for selectively changing a polarization state of light passing through the single imaging path to alternate between forming a first image through the first portion of the single imaging path and forming a second image through the second portion of the single imaging path, the first image representing objects within the field of view from the first perspective viewpoint and the second image representing the objects from the second perspective viewpoint, the first and second images together being operable to represent three dimensional spatial attributes of the objects.

In accordance with another aspect of the invention there is provided an apparatus for generating three-dimensional image information. The apparatus includes a lens having a single imaging path operable to direct light captured within a field of view of the lens to an aperture plane of the lens, an optical element located proximate the aperture plane, the optical element including a first portion disposed to transmit light having a first state through a first portion of the single imaging path and a second portion disposed to transmit light having a second state through a second portion of the simile imaging path, the first and second portions of the single imaging path providing respective first and second perspective viewpoints within the field of view of the lens. The apparatus also includes a modulator disposed in the single imaging path, the modulator being operable to selectively change a state of light passing through the modulator to alternate between forming a first image through the first portion of the single imaging path and forming a second image through the second portion of the single imaging path, the first image representing objects within the field of view from the first perspective viewpoint and the second image representing the objects from the second perspective viewpoint, the first and second images together being operable to represent three dimensional spatial attributes of the objects.

The first portion of the optical element may include a polarizer disposed to transmit light having a first polarization state through the first portion of the single imaging path and the second portion of the optical element may include a polarizer disposed to transmit light having a second polarization state through the second portion of the single imaging path and the modulator may be operable to selectively change a polarization state of light passing through the modulator to alternate between the first polarization state and the second polarization state.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
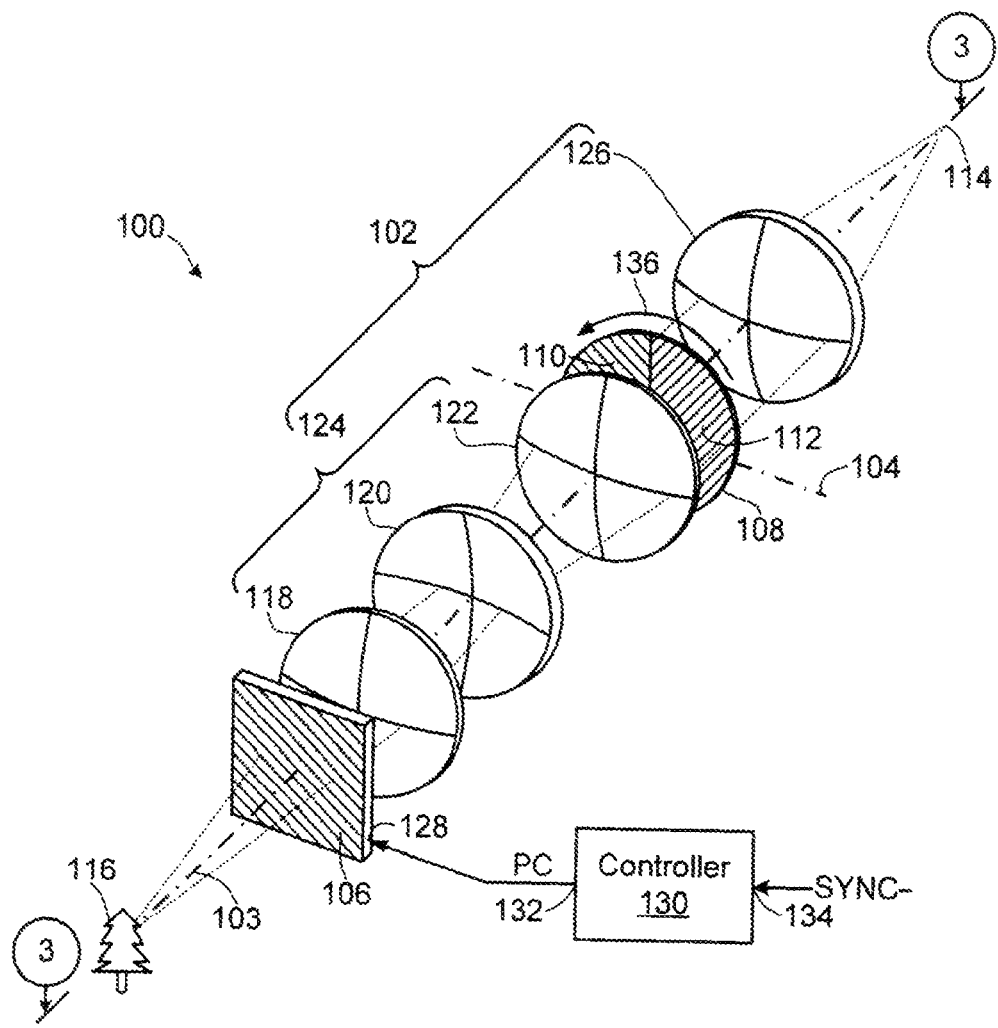
FIG. 1 is a perspective view of an apparatus for generating three-dimensional image information according to a first embodiment of the invention.

Referring to FIG. 1, en apparatus for generating three-dimensional image information according to a first embodiment of the invention is shown generally at 100. The apparatus 100 includes a lens 102 having a single imaging path generally oriented along a central axis 103. The lens 102 is operable to direct light captured within a field of view of the lens to an aperture plane 104 of the lens.

The apparatus 100 also includes a polarizer 108 located proximate the aperture plane 104. The aperture plane 104 may be a physical aperture plane of the lens 102 or may be a conjugate of the aperture plane. The polarizer 108 includes a first portion 110 disposed to transmit light having a first polarization state through a first portion of the single imaging path and a second portion 112 disposed to transmit light having a second polarization state through a second portion of the single imaging path. The first and second portions of the single imaging path provide respective first and second perspective viewpoints within the field of view of the lens 102.

The apparatus 100 further includes a modulator 106 disposed in the single imaging path. The modulator 106 is selectively operable to change a polarization state of light passing through the modulator to alternate between forming a first image through the first portion of the single imaging path and forming a second image through the second portion of the single imaging path. The first image represents an object (such as the object 116) within the field of view from the first perspective viewpoint and the second image represents the object from the second perspective viewpoint. The first and second images are together operable to represent three-dimensional spatial attributes of the object 116.

In the embodiment shown in FIG. 1, the lens 102 includes a plurality of lens elements including lens elements 118, 120, and 122, which make up a zoom lens group 124 and define the location of the aperture plane 104. The focal length of the zoom lens group 124 may be varied by moving lens elements 118 and 120. The lens 102 also includes a focusing lens 126 for focusing the images at the image plane 114. In other embodiments, the lens 102 may be made of a greater or lesser number of lens elements and may be a prime, telephoto, or other type of lens used in imaging.

The modulator 106 includes an input 128 for receiving a control signal for selectively causing the modulator to change the polarization state of the light passing through the modulator. The apparatus 100 also includes a controller 130 having an output 132 for producing the control signal. The controller 130 also includes an input 134 for receiving a synchronization signal (SYNCH), which may be received from control circuitry associated with an image recording element such as a charge coupled device (not shown) disposed at the image plane 114 for recording the first and second images. The modulator 106 may be implemented using a liquid crystal device, Faraday rotator, or other electro-optic device that is operable to change a polarization state of light passing through the device in response to receiving a control signal or drive signal. Alternatively, the modulator 106 may be implemented by mechanically moving a polarizing element as detailed later herein.

In one embodiment, the first portion 110 of the polarizer 108 may be implemented using a linear polarizer having a first linear polarization orientation and the second portion 112 of the polarizer 108 may be implemented using a linear polarizer having a second linear polarization orientation, the first linear polarization orientation being orthogonal to the second linear polarization orientation. In the embodiment shown in FIG. 1, the first and second polarization orientations are respectively at +45° and −45° to vertical but in other embodiments the polarizations may be otherwise oriented (e.g. vertically and horizontally). Advantageously, orienting the first and second polarization orientations at ±45° prevents differences between the first and second images due to light received from the field of view of the lens 102 being partially polarized, as would occur when light reflects off surfaces such as a roadway or body of water, for example.

In another embodiment, the first portion 110 of the polarizer 108 may include a polarizer operable to transmit light having a left-handed elliptical polarization state and the second portion 112 of the polarizer 108 may include a polarizer operable to transmit light having a right-handed elliptical polarization state. Alternatively, the first and second portions 110 and 112 of the polarizer 108 may include materials operable to transmit light having respective left-handed circular polarization and right-handed circular polarization states.

When oriented as shown in FIG. 1, the apparatus 100 is configured to generate images in what is commonly referred to as "landscape orientation" (i.e. the longest dimension of the image is horizontally oriented). The resulting first and second images are separated into right and left images, which advantageously causes the first and second images to correspond to images that would usually be viewed by a user's horizontally separated right and left eyes. However, particularly in still image photography, it is common for users of a camera to capture images in both landscape orientation and portrait orientation (i.e. where the longer dimension of the image is vertically oriented). In an alternative embodiment of the apparatus 100, the apparatus may be configured to permit configuration in either a landscape mode or a portrait mode. Specifically, the polarizer 108 may be rotated by 90 degrees in the direction indicated by the arrow 136, such that the first and second images are vertically separated in the orientation of the apparatus as shown in FIG. 1. In this configuration, when the apparatus 100 is oriented to capture images in portrait mode, the first and second images would remain horizontally separated, thus providing first and second images having respective right and left perspective viewpoints. The 90 degree rotation of the polarizer 108 may be implemented using a mechanical rotator having an actuator that is manually operated by the user. Alternatively, the mechanical rotator may be actuated by an electric motor either in response to user selection of a portrait mode, or automatically in response to an orientation signal generated by an orientation sensor such as an accelerometer or gravity sensor (not shown).

Modulator

Figure 2:
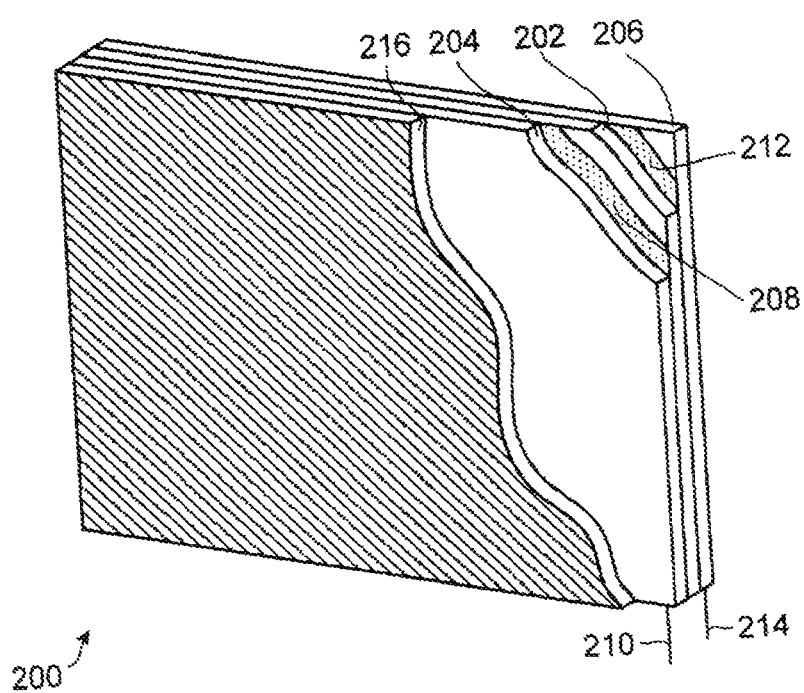
FIG. 2 is a partially cut away perspective view of a liquid crystal image modulator.

In one embodiment the modulator 106 may be implemented using a liquid crystal to modulate the polarization state of light. Referring to FIG. 2, a liquid crystal image modulator is shown generally at 200. The modulator 200 includes a liquid crystal material layer 202 disposed between a first glass plate 204 and a second glass plate 206. The first glass plate 204 includes a first transparent electrode 208, which extends across a surface of the first glass plate. The second glass plate 206 includes a second transparent electrode 212, which extends across a surface of the second glass plate. The liquid crystal modulator 200 also includes a connector 210 for making an electrical connection to the first transparent electrode 208 and a connector 214 for making an electrical connection to the second transparent electrode 212. The connectors 210 and 214 facilitate application of a drive voltage between the electrodes 208 and 212 to cause an electric field to be established within the liquid crystal layer 202 for changing polarization properties of the liquid crystal material.

The modulator 200 also includes a polarizing layer 216 that permits light of having a first linear polarization orientation to be transmitted. In this case, the first linear polarization orientation is at an angle of −45° to vertical. In other embodiments the first linear polarization orientation may be otherwise oriented, as disclosed earlier herein. In FIG. 2 the thickness of the various layers are not shown to scale.

The liquid crystal layer 202 may be a twisted nematic crystal material, which in the relaxed state with no drive voltage applied between the connectors 210 and 214 causes a rotation of a polarization orientation of light passing through the layer. For example, the liquid crystal may be configured to cause linearly polarized light to undergo a 90° rotation of the polarization orientation in the relaxed state. When a drive signal is applied between the connectors 210 and 214, the twisted nematic crystal material re-orients to permit the light to pass through the layer 202 without changing the polarization orientation. In one embodiment, the liquid crystal layer 202 may be actuated by application of a drive signal having a 50% duty cycle square wave varying between a voltage $V^+$ and $V^-$, where the voltages are selected within a range of safe operating voltages to provide a 90° change to the polarization orientation of the light from a −45° polarization orientation (as received after transmission through the polarizing layer 216) to a +45° polarization orientation. The controller 130 (shown in FIG. 1) may be configured to selectively generate the drive signal when it is desired to actuate the liquid crystal layer 102 to permit the light to pass. In the un-actuated state of the liquid crystal, no drive potential is applied between the connectors 210 and 214. Alternatively, the controller 130 may provide a low level actuation signal that controls a modulator driver (not shown) to selectively generate the drive voltage signal.

For use in embodiments where the modulator 200 is located before the polarizer 108 in the imaging path (as shown in FIG. 1), light impinges on the polarizing layer 216 and only light having a −45° polarization orientation is transmitted to the liquid crystal layer 202. With no drive voltage applied between the connectors 210 and 214 the vertically polarized light undergoes a rotation in polarization orientation and emerges from the liquid crystal layer as light having a +45° polarization orientation. When a drive voltage is applied between the connectors 210 and 214, the light having a −45° polarization orientation is transmitted without any change to polarization orientation. The modulator 200, in this mode of operation thus selectively changes the polarization state of transmitted −45° polarized tight between −45° and +45° in response to application of the drive voltage.

Operation

Figure 3:
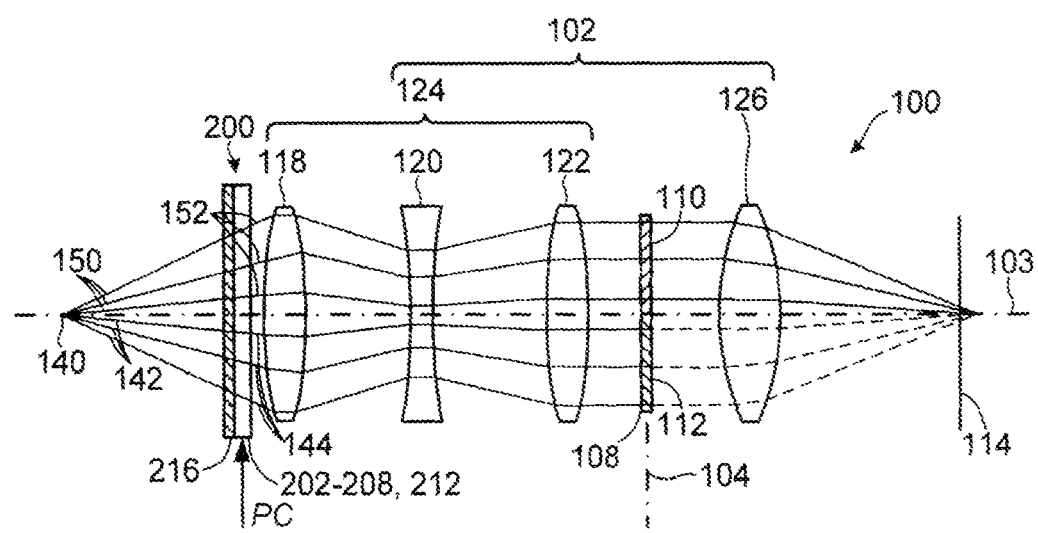
FIG. 3 is a top view depicting an operational state of the of the apparatus shown in FIG. 1.

Operation of the modulator 200 shown in FIG. 2 is described with further reference to FIG. 3, which shows the apparatus 100 in top view. In the embodiments shown, the first portion 110 of the polarizer 108 comprises a linear polarizer operable to transmit light polarized at +45° and to block light polarized at −45°. The second portion 112 of the polarizer 108 comprises a linear polarizer operable to transmit light polarized at −45° and to block light polarized at +45°. The liquid crystal image modulator 200 is configured such that incoming light impinges on polarizing layer 216, which is configured to transmit light polarized at −45° before passing through the liquid crystal layer 202.

Referring to FIG. 3, light rays 150 emanating from a point 140 may include randomly polarized light and light components polarized at −45° are transmitted by the polarizing layer 216, while otherwise polarized light components are blocked. In the operational embodiment shown in FIG. 3, the control signal PC (generated by the controller 130 shown in FIG. 1) has a signal state PC1 that causes the modulator 200 to be in the relaxed state, which causes the liquid crystal layer to change the polarization orientation of the light by 90° from −45° to +45°, such that the light rays 144 and 152 are polarized at +45°. The light rays 152 are captured by the lens 102 and directed to the aperture plane 104 where the rays pass through the first portion 110 of the polarizer 108 and impinge on the image plane 114. Light rays 142 emanating from the point 140 may also include randomly polarized light, and as before only light components polarized at −45° are transmitted through the polarizing layer 216. The light rays 144 emerging from the modulator 200 are thus polarized at +45° and are blocked by the second portion 112 of the polarizer 108 and thus do not reach the image plane 114. The first portion 110 of the polarizer 108 thus defines the first portion of the single imaging path of the lens 102 that is involved in forming a first image.

When the control signal PC changes state to a signal state PC2, the modulator 200 is placed in an activated or untwisted nematic state and light polarized at −45° passing through the polarizing layer 216 is transmitted through the liquid crystal layer 202 without undergoing a change in polarization orientation, thus remaining oriented in a −45° polarization state. The light rays 144 are captured by the lens 102 and directed to the aperture plane 104 where the rays 144 are transmitted through the second portion 112 of the polarizer 108 and impinge on the image plane 114. Light rays 152 are blocked at the first portion 110 of the polarizer 108 and do not reach the image plane 114. The second portion 112 of the polarizer 108 thus defines the second portion of the single imaging path of the lens 102 that is involved in forming a second image.

When the first and second images are selectively directed to respective left and right eyes of a user, the user will be able to discern 3D information from the images, in much the same way that the user would be able to discern 3D information when viewing the actual object 116.

In another embodiment, the first and second images may be alternately displayed as separate video fields on a video display monitor. Various types of active and passive eyewear are available for directing such displayed first and second images to the user's eyes. Passive types of eyewear generally rely on additional wavelength or polarization processing of the displayed images to enable passive filter elements in the eyewear to separate the images. Active types of eyewear generally include a receiver for receiving a synchronization signal from a display to alternatively permit transmission of the first and second images to the respective left and right eyes. Alternatively, the first and second images may be processed to match up identifiable features in the respective images and to determine lateral shifts between the identified features. The determined lateral shifts, along with knowledge of the imaging parameters of the apparatus 100, may be used to calculate a difference in depth between points on an object or between objects at different depths.

Advantageously, the polarizer 108 may be a passive polarizer element, which permits use of relatively thin materials such as an absorptive polarizer film or thin film polarizer. Such materials permit the polarizer 108 to be placed very close to or at the aperture plane 104, even in a lens 102 that has limited space between lens elements. It is advantageous to have selective transmission/blocking of the light for producing the first and second images occurring at least proximate an aperture plane of the lens 102 to reduce or eliminate vignetting of the images due to the selective transmission of light through the first or second portions of the single imaging path. In some embodiments, the polarizer may be located proximate an iris (not shown) of the lens that defines the system aperture and controls an amount of light captured by the lens 102. Alternatively, the first and second portions 110 and 112 of the polarizer 108 may be applied directly as a coating to a lens element defining an aperture plane of a lens, or a lens element that is located proximate the aperture plane of the lens.

To achieve a desired imaging quality or performance using a particular lens, an optical sensitivity analysis may be performed to yield a distance tolerance representing a maximum displacement of the polarizer 108 from the aperture plane 104. Such an analysis may take into account geometric offsets in the first and second images due to vignetting due to the first and second portions 110 and 112 of the polarizer 108, and the distance tolerance would provide a maximum distance from the aperture plane to satisfy a criterion for acceptable 3D imaging quality. The degree to which imaging quality is affected by moving the polarizer 108 away from the aperture plane is dependent on the configuration of the lens elements making up the lens 102 and the desired imaging performance of the system. In very high performance imaging systems, the polarizer 108 may have to be located very close to the aperture plane 104 to minimize vignetting and thus provide first and second images having substantially uniform image intensity across the image. In lower performance imaging systems, it may be acceptable to permit quite significant image intensity falloff at edges of the images since the human eye is not extremely sensitive to such falloff. In non-critical imaging applications a 30% to 50% image falloff at the outer edges of an image may be acceptable.

Modulators, such as the liquid crystal modulator 200 are generally thicker in the direction of light transmission and thus may not be easily accommodated at the aperture plane. Advantageously the modulator 200 may be located at any of a number of locations within the lens 102. In this embodiment, the modulator 106 is located in front of the lens 102, but in other embodiments an appropriately configured modulator could equally well be located between any of the lens elements, or between the focusing lens 126 and the image plane 114, for example.

A modulator that operates as an active polarizing element may be characterized in terms a ratio of intensities between light having respective first and second polarization states. As a practical matter, for many active polarizing elements the polarization ratio falls off when a convergence or divergence angle of light impinging on the polarizer is greater than an angle of acceptance criteria associated with said modulator. In such embodiments it may be desirable to locate the modulator 200 at a point in the single imaging path where the convergence or divergence angle of the captured light is less than an angle of acceptance criteria associated with said modulator. In some embodiments the lens 102 may have a region over which the light is close to being collimated, which provides a generally optimal location for the modulator 200, subject to other spacing and design constraints associated with the particular lens. In the embodiments shown in FIGS. 1 and 3 as long as the object 116 is located far away from the lens 102, light entering the modulator 200 would have generally low angular incidence.

Alternatively, for use in embodiments where the liquid crystal modulator 200 is located in a reversed orientation after the polarizer 108 in the imaging path, light having a +45° polarization orientation is transmitted through the first portion 110 of the polarizer 108 and light having a −45° polarization orientation is transmitted through the second portion 112 of the polarizer. When the control signal PC is in the first state PC1 the liquid crystal layer is in the relaxed nematic state and light of both −45° and +45° polarization orientations will undergo a rotation in polarization orientation. Light having a polarization orientation of +45° from the first portion 110 of the polarizer 108 will be rotated to have a polarization orientation of −45° will thus be transmitted through the polarizing layer 216 to the imaging plane 114 forming the first image. The light having a polarization orientation of −45° from the second potion 112 of the polarizer 108 will be rotated to a +45° polarization orientation and will be blocked by the polarizing layer 216. When the control signal PC changes state to PC2, the liquid crystal in the un-twisted nematic state passes light having either a −45° or +45° polarization orientation without change to polarization orientation and the −45° polarized light is transmitted through the polarizing layer 216 to the image plane 114 forming the second image. The +45° polarized light from the first portion 110 of the polarizer 108 will be blocked by the polarizing layer 216.

Spatial Modulator Embodiment

Figure 4:
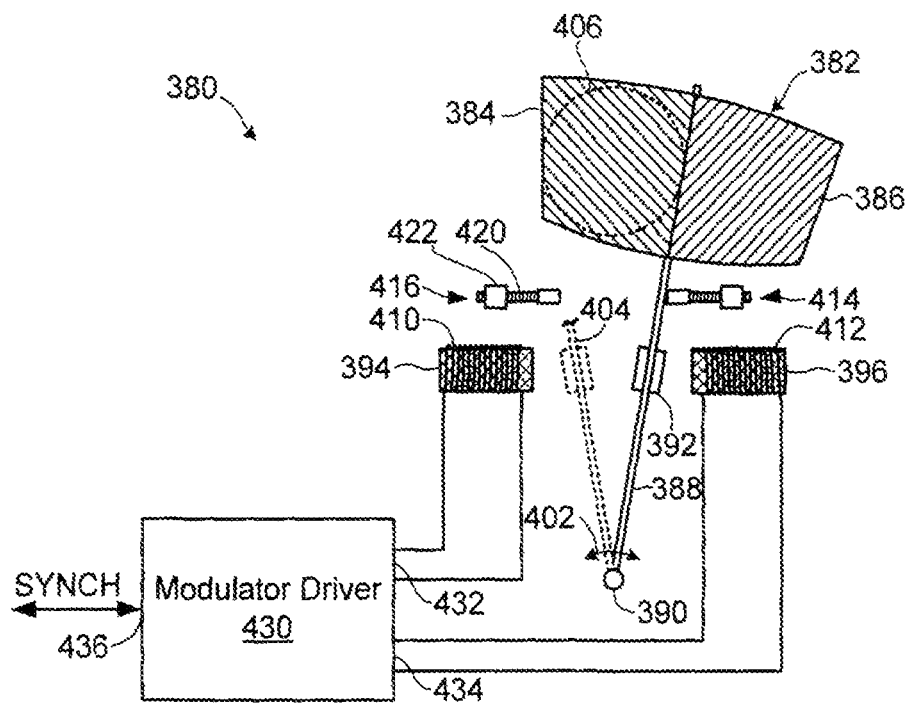
FIG. 4 is a plan view of a spatial modulator embodiment for implementing the apparatus shown in FIG. 1.

In an alternative embodiment the modulator 106 shown in FIG. 1 may be implemented using the spatial modulator shown generally at 380 in FIG. 4. Referring to FIG. 4, the spatial modulator 380 includes a polarizer 382 having a first region 384 operable to transmit light having a +45° polarization orientation and a second region 386 operable to transmit light having a −45° polarization orientation. The polarizer 382 is mounted on an arm 388, which in turn is mounted on a pivot 390 to provide side-to-side motion of the spatial modulator 380. The arm 388 also includes a magnet 392 mounted partway along the arm. The magnet 392 is disposed between first and second electromagnets 394 and 396 having respective coils 410 and 412. The polarizer 382, arm 388, pivot 390, and the electromagnets 394 and 396, together make up a mechanical actuator operable to produce a force for moving the polarizer 382 from side-to-side in the direction of the arrow 402 between a first arm position (as shown in solid outline) and a second position (shown in broken outline at 404). In this embodiment the first and second arm positions are defined by a pair of stops 414 and 416, which respectively define first and second positions of the arm and the polarizer 382. The stops 414 and 416 each comprise a threaded portion 420 that engages a complimentary threaded portion 422 to provide for adjustment of movement of the arm 388 and polarizer 382.

An extent of the single imaging path of a lens (such as the lens 102 shown in FIG. 1) is shown in broken outline at 406. In the first arm position, the first polarizing region 384 is disposed to permit light having a +45° polarization orientation to pass through the single imaging path while blocking light having a −45° polarization orientation. In the second arm position 404, the second polarizing region 386 is disposed to permit light having a −45° polarization orientation to pass through the single imaging path while blocking light having a +45° polarization orientation.

For driving the spatial modulator 380, the modulator driver 130 shown in FIG. 1 may be replaced by the modulator driver 430 shown in FIG. 4. The modulator driver 430 includes a first pair of outputs 432 for driving the coil 410 of the first electromagnet 394 and a second pair of outputs 434 for driving a coil 412 of the second electromagnet 396.

The modulator driver 430 also includes an output 436 for producing a synchronization signal (SYNC) for synchronizing operation of an image sensor to capture the first and second images. Alternatively, the output 436 may be configured as an input for receiving a synchronization signal generated by an image sensor to facilitate synchronization of the motion of the arm 388 with a pre-determined image capture rate of an image sensor. In operation, the modulator driver 430 either generates the SYNCH signal internally, or receives the SYNC signal at the input 436. In response to the SYNCH signal, the controller generates current waveforms at the outputs 432 and 434 for driving the respective coils 410 and 412. The current through the respective coils 410 and 412 cause forces to be exerted on the arm 388 to move toward a desired stop 414 or 416. Advantageously, the modulator driver 430 may be implemented as a push-pull controller where one of the electromagnets 304 and 396 provides an attractive force on the magnet 392, while the other of the electromagnets provides a repulsion force on the magnet, thus increasing the force on the arm while moving between stops 416 and 414.

Figure 5:
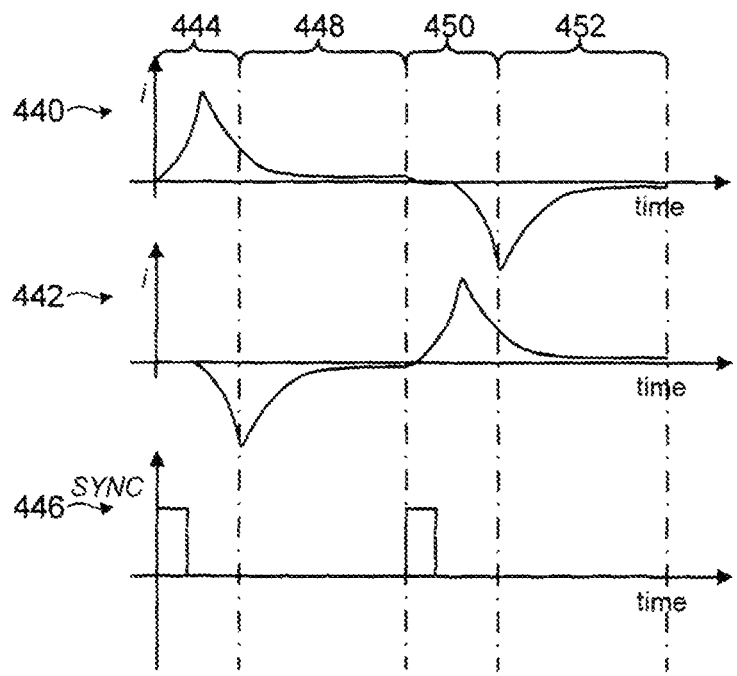
FIG. 5 is a series of graphs depicting current waveforms for controlling the spatial modulator shown in FIG. 4.

Exemplary waveforms of a current drive provided to the coils 410 and 412 to cause the arm 388 to move toward the first electromagnet 394 are shown graphically in FIG. 5. The current waveform through the coil 410 is shown at 440 and the current waveform through the coil 412 is shown at 442. The SYNCH signal pulse waveform is shown at 446. A rising edge of the SYNCH signal 446 defines a start time of a first time period 444, in which the current 440 rises rapidly to produce an attractive force on the arm 388. The attractive force overcomes the inertia of the arm 388 and causes the arm to accelerate away from the stop 414 and the second electromagnet 306. During the first time period 444 the current 442 is initially at zero and once the arm 388 begins to accelerate, the current 442 increases rapidly to provide a decelerating force as the arm approaches the stop 416, thereby damping the motion of the arm to prevent bouncing of the arm when engaging the stop. The arm 388 comes to rest at the stop 416 and the currents 440 and 442 reduce to a small holding current in each of the coils 410 and 412 to hold the arm at the stop 416. A second time period 448 during which the arm 388 is held at the stop 416 provides sufficient time to complete capture of the first image.

Similarly, a subsequent rising edge of the SYNCH signal 446 defines a start time of a third time period 450, in which the current 442 causes an attractive force and the current 440 a repulsion force on the arm 388 to cause the arm to move toward the stop 414. A time period 452 during which the arm 388 is at rest at the stop 414 defines a fourth time period 452, which provides sufficient time to complete capture of the second image.

Figure 6:
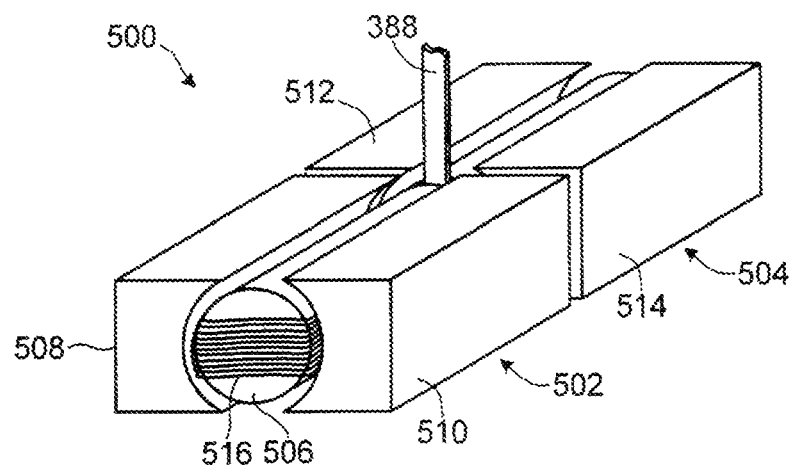
FIG. 6 is a perspective view of an alternative actuator for the spatial modulator shown in FIG. 4.

Referring to FIG. 6, an alternative embodiment of the actuator portion of the spatial modulator 380 (shown in FIG. 4) is shown generally at 500. The actuator 500 includes a motor 502 having a rotor shaft 506 extending through the motor. The arm 388 is mounted to the shaft 506 for side-to-side motion as generally shown in FIG. 4. In this embodiment, the motor 502 is implemented using a pair of magnets 508 and 510 and the shaft 506 supports an actuator coil 516 between the magnets. The actuator coil 516 is coupled to the modulator output 432 for receiving a drive current, which causes a torque to be generated on the shaft 506. In general, the actuator 500 operates in a manner similar to an analogue meter movement and provides movement between stops 414 and 416. In other embodiments, the motor portion 502 may be configured such that the shaft 506 is magnetized and the coil is wound around pole pieces (i.e. 508 and 510).

Variable Steropsis

In the embodiment shown in FIG. 1, the single imaging path is circular in shape and the first portion 110 of the polarizer 108 extends to cover a first semicircular portion of the imaging path, while the second portion 112 extends to cover a second semicircular portion of the imaging path.

Figure 7:
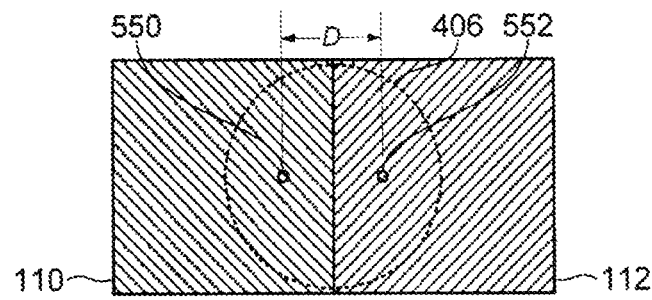
FIGS. 7-9 are a series of views showing an alternative embodiment of a polarizer used in the apparatus shown in FIG. 1.
Figure 8:
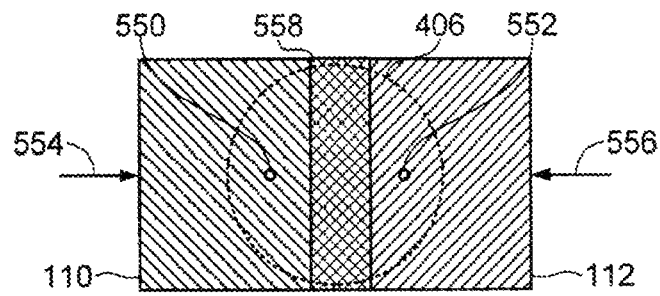
Figure 9:
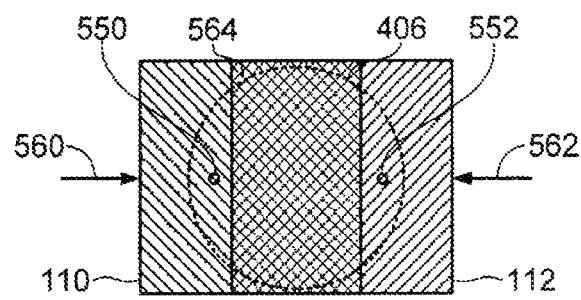

In an alternative embodiment, the first and second portions 110 and 112 may each extend to cover a sector of the single imaging path of less then a semicircular area as shown in FIG. 7, FIG. 8 and FIG. 9. Referring to FIG. 7, the polarizer 108 is sized such that the first and second portions 110 and 112 extend outwardly beyond the imaging path 406. A centroid of the area of the single imaging path (indicated by broken line 406) covered by the first portion 110 is shown at 550 and a centroid of the area of the single imaging path covered by the second portion 112 is shown at 552. The centroids 550 and 552 may be viewed as defining a center of perspective for the respective first and second images formed through a lens, such as the lens 102 shown in FIG. 1. A distance D between the two centroids 550 and 552 represents the steroptic separation between images, which loosely equates to an "amount of 3D" generated by the apparatus.

Referring to FIG. 8, by moving the first portion 110 of the polarizer 108 inwardly in the direction of the arrow 554 and the second portion 112 inwardly in the direction of the arrow 556, an overlapping region 558 is formed between the two polarizer portions. Light passing through the overlapping region 558 will pass through both a portion of the polarizer 108 having a −45° polarization orientation and a portion having a +45° polarization orientation and will thus be blocked regardless of polarization orientation. Under these conditions the centroids 550 and 552 are each shifted outwardly and thus the perspective viewpoint is also shifted outwardly providing greater steroptic separation between the first and second images.

Referring to FIG. 9, further movement of the first portion 110 of the polarizer 108 inwardly in the direction of the arrow 560 and the second portion 112 inwardly in the direction of the arrow 562, causes the overlapping region 564 between the two polarizer portions to increase in extent. Light passing through the overlapping region 564 will again pass through both −45° and +45° polarizing portions of the polarizer 108 and will thus be blocked. Under these conditions the centroids 550 and 552 are again shifted outwardly thus further changing the perspective viewpoint.

In one embodiment, the movements of the portions 110 and 112 of the polarizer 108 may be performed by an actuator such as a mini stepper motor and the degree of separation of the centroids may be varied while the first and second images are being formed to provide for variable steropsis as disclosed in commonly owned PCT patent application PCT/CA2009/000957, filed on Jul. 10, 2009, entitled "METHOD AND APPARATUS FOR GENERATING THREE DIMENSIONAL IMAGE INFORMATION USING A SINGLE IMAGING PATH", which is incorporated herein by reference in its entirety.

Circular Polarization Embodiment

Figure 10:
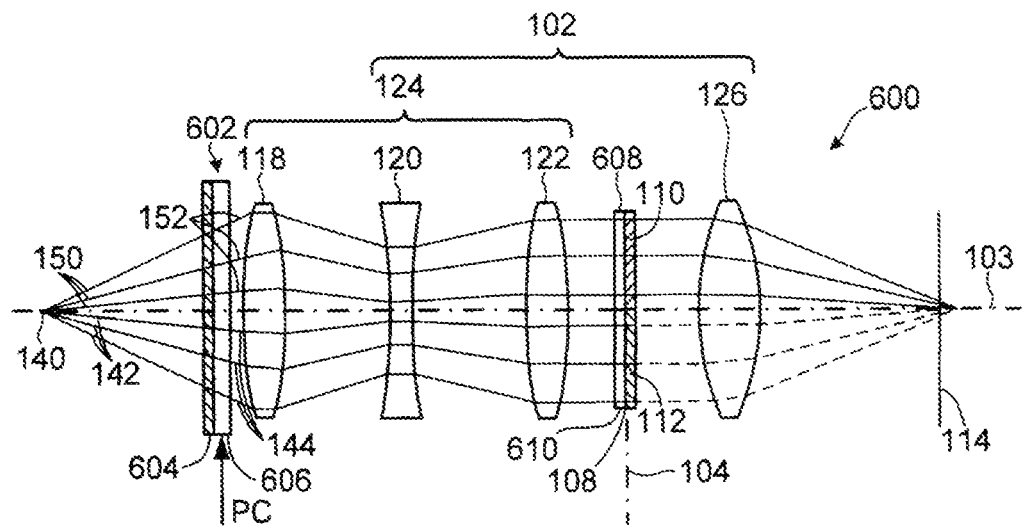
FIG. 10 is a top view of an apparatus for generating three-dimensional image information according to another embodiment of the invention.

While the above embodiments have been described in connection with linear polarization orientations, the modulator 200 above may also be configured to operate on elliptically or circularly polarized light. Referring to FIG. 10, a circular polarization embodiment is shown generally at 600. In this embodiment a modulator 602 is disposed in front of the lens element 118 and includes a linear polarizing layer 604 that transmits light having a polarization orientation of −45°. The modulator 602 also includes a liquid crystal layer 606 that is configured to selectively switch between a +90° phase retardation and a −90° phase retardation to produce either right hand circular polarized light or left hand circular polarized light.

The first and second portions 110 and 112 of the polarizer 108 are linear polarizers operable to respectively transmit light having +45° and −45° polarization orientations. The polarizer 108 further includes a first quarter wave plate 608, which is oriented to cause light having a right-hand circular polarization to be converted into linearly polarized light at an orientation of +45°, which is transmitted through the portion 110 of the polarizer 108. The polarizer 108 also includes a second quarter wave plate 610, which is oriented to cause light having a left-hand circular polarization to be converted into linearly polarized light at an orientation of −45°, which is transmitted through the portion 112 of the polarizer 108. The first and second portions 110 and 112 of the polarizer 108 thus cause the first and second images to be formed at the image plane 114 as described earlier herein.

Non-Polarizing Embodiment

Figure 11:
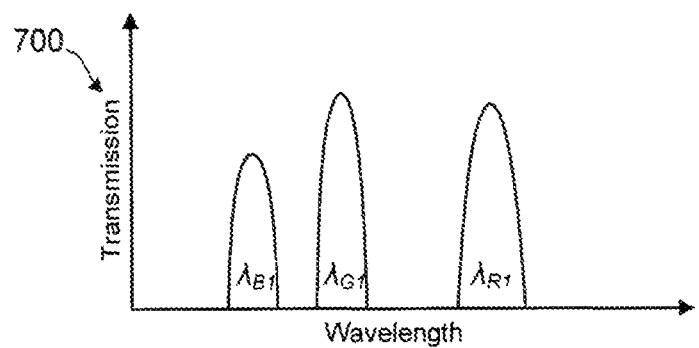
FIG. 11 is a graphical depiction of transmission spectra for interference filters used in yet another embodiment of the invention.
Figure 11:
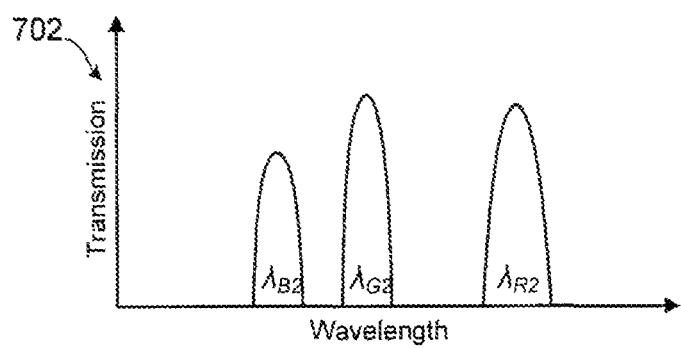

In other embodiments the polarizer portions 110 and 112 of the polarizer 108 in FIG. 2 may be replaced with filter portions that operate on another property of the light to generate the first and second images. For example, the portions 110 and 112 may be interference filters that transmit specific narrow bands of light wavelengths, such as blue, green, and red light. Transmission spectra for such interference filters are shown graphically in FIG. 11 at 700 and 702. Referring to FIG. 11, the filter 110 may be configured to transmit a first plurality of light wavelengths $\lambda_{B1}$, $\lambda_{G1}$, and $\mu_{R1}$ as shown at 700 and the filter 112 may be configured to pass a second plurality of light wavelengths $\mu_{B2}$, $\mu_{G2}$, and $\mu_{R2}$ as shown at 702. A spatial modulator, such as the modulator shown in FIG. 4, may be configured such that the first region 384 transmits the first plurality of wavelengths 700 while second region 386 transmits the second plurality of wavelengths 702. In operation, the spatial modulator alternates to permit the first and second wavelength ranges to be selectively received though the single imaging path. When the second plurality of wavelengths 702 are received through the single imaging path, the interference filter portion 110 blocks these wavelengths while the interference filter portion 112 transmits the second plurality of wavelengths, which are imaged to form a first image at the image plane 114. When the first plurality of wavelengths 700 are received through the single imaging path, the interference filter portion 112 blocks these wavelengths while the interference filter portion 110 transmits the first plurality of wavelengths, which are imaged to form a second image at the image plane 114. Since the human eye includes receptors that are not very sensitive to slight shifts in wavelength, the images discerned by the left and right eyes will not be significantly different in spectral or colour appearance, but have different perspective viewpoints provided by the first and second portions of the single imaging path. The first and second pluralities of wavelengths would be sufficiently different such that the respective transmission bands have an insignificant overlap. For example, wavelength differences in the region of 10 nanometers are virtually indiscernible by the human eye as long as there is not a significant intensity disparity between the wavelengths. Since the receptors in the human eye are not sensitive to such small shifts, the first and second images received by the eyes are not perceived as having a different spectral or color content.

Circular Polarization Input Embodiment

Figure 12:
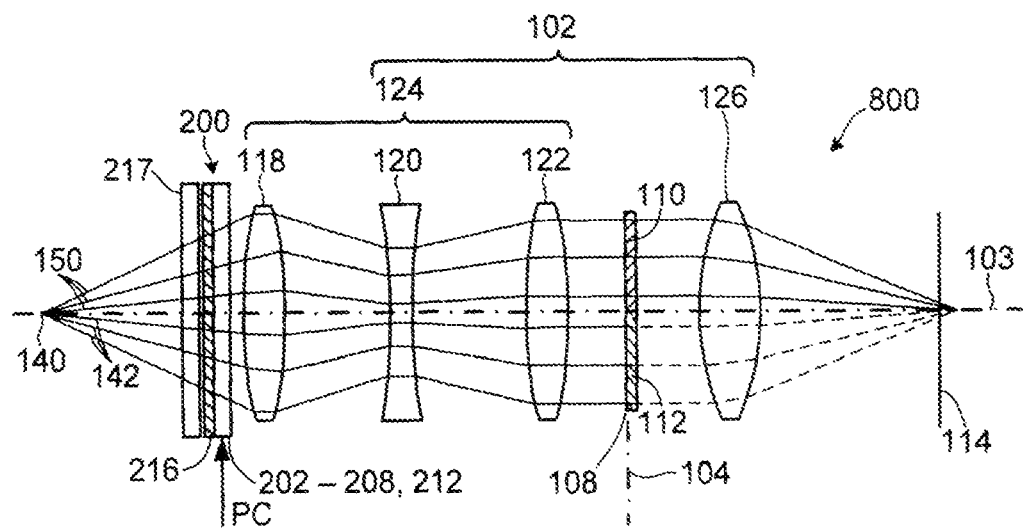
FIG. 12 is a top view of an apparatus for generating three-dimensional image information according to a further embodiment of the invention.

While the above embodiments have been described in connection with linear polarization orientations, in other embodiments the apparatus may be configured to operate on elliptically or circularly polarized light. Referring to FIG. 12, a circular polarization input embodiment of the apparatus is shown generally at 800. In this embodiment the modulator 200 is disposed between the lens element 118 and the point 140 in the field of view of lens 102 at an input end of the apparatus 800. The modulator 200 includes the linear polarizing layer 216 that transmits light having a polarization orientation of −45°. A quarter wave plate 217 is arranged between the polarizing layer 216 and the point 140 so that incoming circularly and elliptically polarized light is rendered linearly polarized by transmission through the quarter wave plate 217. Only the −45° component of that transmitted linear polarized light is transmitted further by the polarizing layer 216. The modulator 200 operates as described before and alternately renders the transmitted light +45° polarized, when it is under the control of the control signal PC in its PC1 relaxed state, and −45° polarized, when it is under the control of the control signal PC in its PC2 activated state.

In this embodiment, the first and second portions 110 and 112 of the polarizer 108 are linear polarizers operable to respectively transmit light having +45° and −45° polarization orientations. The first and second portions 110 and 112 of the polarizer 108 thus cause first and second images to alternately be formed at the image plane 114 as described earlier herein. Light having a first polarization state transmitted through the first portion 110 of the single imaging path of the apparatus 800 provides a first perspective viewpoint within the field of view of the lens 102. Light having a second polarization state transmitted through the second portion 112 of the single imaging path of apparatus 800 provides a second perspective viewpoint within the field of view of the lens 102. The first and second portions 110 and 112 of the polarizer 108 thus cause the first and second images to be formed at the image plane 114 as described earlier herein. The first image represents objects within the field of view of the lens 102 from the first perspective viewpoint and the second image represents the objects from a second perspective viewpoint, the first and second images together being operable to represent three-dimensional spatial attributes of the objects.

Circular Polarization Output Embodiment

Figure 13:
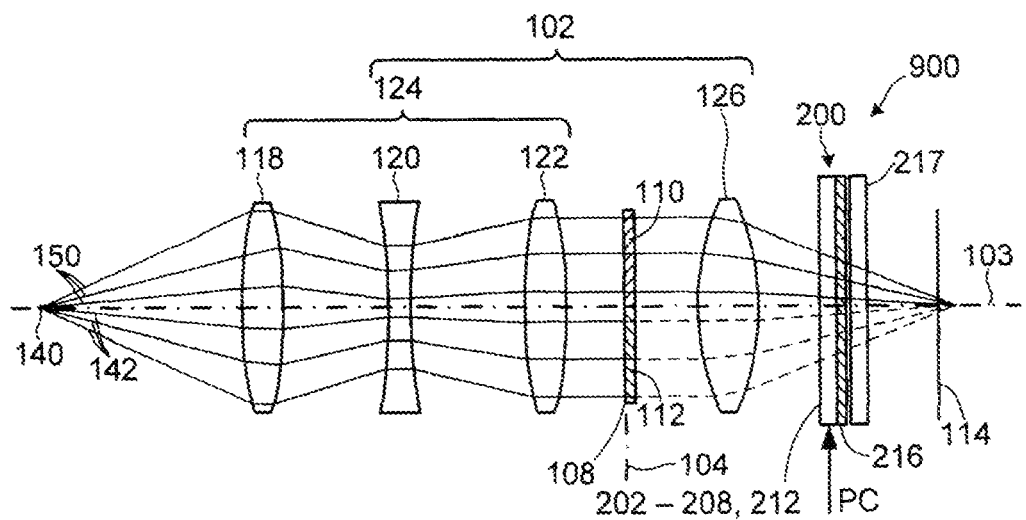
FIG. 13 is a top view of an apparatus for generating three-dimensional image information according to yet another embodiment of the invention.

In an alternative embodiment of the present invention, shown generally at 900 in FIG. 13, the modulator 200 is disposed between lens 126 and the image plane 114 with the polarizing layer 216 facing image plane 114 at an output end of the apparatus 900. A quarter wave plate 217 is disposed between the polarizing layer 216 and the image plane 114. In this embodiment light rays 150 that pass through the portion 110 of the polarizer 108 have a +45° linear polarization upon emerging from the polarizer, while light rays 142 that pass through the portion 112 of the polarizer have a −45° linear polarization upon emerging from the polarizer.

When the modulator 200 is in the PC1 relaxed state, it changes the polarization of the rays 150 by 90° to +135°, while it changes the polarization of the rays 142 by 90° to +45°. The polarization of +135° is operationally equivalent to −45° in respect of the working of the polarizing layer 216, which transmits only light of polarization parallel to −45°. Therefore, when the rays 150 and 142 impinge on the polarizing layer 216, only the rays 150 are transmitted to the quarter wave plate 217 and the rays 142 are stopped. The quarter wave plate 217 renders the rays 150 circularly polarized.

When the modulator 200 is in its PC2 activated state it does not change the polarization of the rays 150, leaving them at +45° linear polarization, while it leaves the polarization of the rays 142 at −45°. When the rays 150 and 142 impinge on polarizing layer 216, only the rays 142 are transmitted to the quarter wave plate 217. The quarter wave plate 217 then renders the rays 150 circularly polarized in the same circular state as the rays 150 when the modulator 200 is in the PC1 relaxed state.

By this mechanism light rays 150 and 142 alternately form an image at the image plane, representing respectively light traveling through the portion 110 and the portion 112 of polarizer 108. Light having a first polarization state through the first portion 110 of the single imaging path of the apparatus 900 provides a first perspective viewpoint within the field of view of the lens 102. Light having a second polarization state through the second portion 112 of the single imaging path of the apparatus 900 provides a second perspective viewpoint within the field of view of the lens 102. The first and second portions 110 and 112 of the polarizer 108 thus cause the first and second images to be formed at the image plane 114 as described earlier herein. The first image represents objects within the field of view of the lens 102 from the first perspective viewpoint and the second image represents the objects from a second perspective viewpoint, the first and second images together being operable to represent three-dimensional spatial attributes of the objects. In both cases the images are formed using circularly polarized light. This may be advantageous for devices such as range finders and certain imaging devices, such as modern SLR cameras, that specifically or preferentially use incoming circularly polarized light. This allows the apparatus 900 to be coupled as an input front-end to such imaging devices and range finders.

Figure 14:
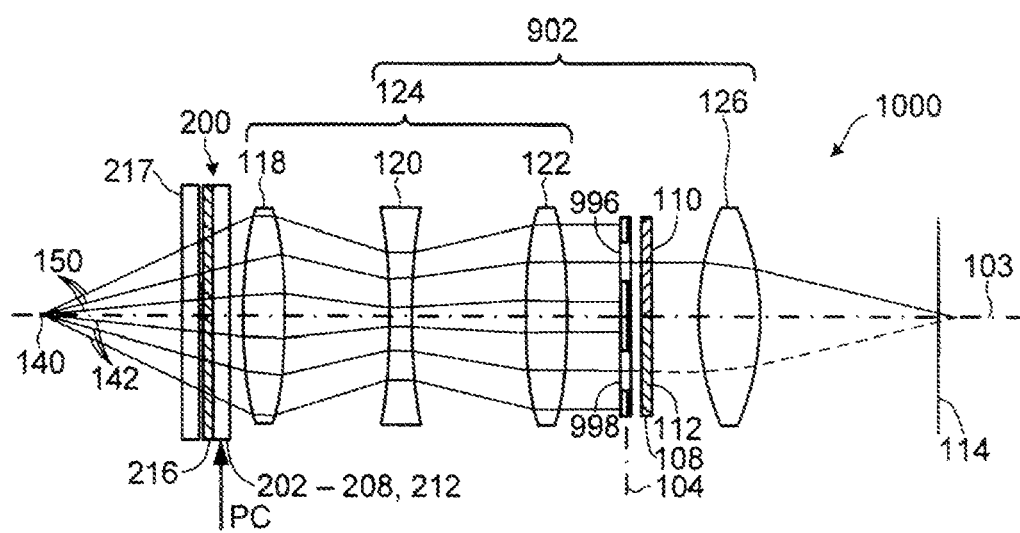
FIG. 14 is a top view of an apparatus for generating three-dimensional image information according to another alternative embodiment of the invention.

A further embodiment of the present invention that may be implemented in all of the aforementioned embodiments involves the addition of a pair of variable stops. Referring to FIG. 14, an exemplary embodiment based on the embodiment described in FIG. 12 is shown generally at 1000. The apparatus 1000 includes a lens 902 having a pair of variable stops 996 and 998 disposed proximate the polarizer 108 as part of the lens. In this embodiment the variable stops 996 and 998 are disposed in front of the polarizer 108 in the single imaging path. Advantageously, the variable stops 996 and 998 may be disposed at the physical aperture of the lens 902 on the aperture plane 104 or at a location of a conjugate of the physical aperture, and polarizer 108 may be disposed to receive light transmitted through the variable stops. In one embodiment, the variable stops 996 and 998 may be implemented as irises. In general the variable stops 996 and 998 may be any arrangement that allows the apertures of stops 996 and 998 to be adjusted, and the apertures may have an oval, rectangular, square, or other shape. All the other elements of lens 902 are as described above for the lens 102 shown in FIG. 12 and the modulator 200 is disposed in front of the lens 902 as described in connection with FIG. 12. The quarter wave plate 217 is disposed in front of the modulator 200, as described earlier herein.

In operation, the variable stops 996 and 998 may be adjusted to change a depth of focus of the apparatus 1000, in one embodiment the variable stops 996 and 998 may be adjusted independently of each other, which facilitates independent adjustment of the depth of focus of the apparatus 1000 for the first portion of the single imaging path and for the second portion of the single imaging path. Other embodiments may provide for corresponding adjustments of the stops such that the depths of focus for each of the first and second portions of the imaging path are substantially matched.

Advantageously, the embodiments described herein facilitate the generation of 3D image information through a single imaging path and are particularly useful in imaging system where the aperture plane is located so as to preclude use of a thick modulating element at the aperture plane. The described embodiments are also useful in imaging systems that are sensitive to vignetting and would require precise placement of a modulator element proximate the aperture plane.

While specific embodiments of the invention have been described and illustrated, such embodiments should be considered illustrative of the invention only and not as limiting the invention as construed in accordance with the accompanying claims.

What is claimed is:

1. An apparatus for generating three-dimensional image information, the apparatus comprising:
a lens having a single imaging path operable to direct light captured within a field of view of the lens to an aperture plane of the lens;
a polarizer located proximate said aperture plane, said polarizer including a first portion disposed to transmit light having a first polarization state through a first portion of the single imaging path and a second portion disposed to transmit light having a second polarization state through a second portion of the single imaging path, said first and second portions of said single imaging path providing respective first and second perspective viewpoints within the field of view of the lens, wherein said first portion of said polarizer comprises a first polarizer having a first polarization orientation and wherein said second portion of said polarizer comprises a second polarizer having a second polarization orientation, said first and second polarization orientations comprise any one of: respective linear polarization orientations that are orthogonal, respective left-handed and right-handed elliptical polarization orientations, and respective left-handed and right-handed circular polarization orientations; and
a modulator disposed in the single imaging path, said modulator being operable to selectively change a polarization state of light passing through the modulator to alternate between forming a first image through said first portion of said single imaging path and forming a second image through said second portion of said single imaging path, said first image representing objects within the field of view from said first perspective viewpoint and said second image representing said objects from said second perspective viewpoint, said first and second images together being operable to represent three dimensional spatial attributes of said objects, wherein said modulator is disposed in the single imaging path before said polarizer, wherein said modulator is operably configured to: select one of said first and second polarization states for transmission, and alternate between: transmitting the selected polarization state; and causing said selected polarization state to undergo a change between said first polarization orientation and said second polarization orientation.

2. The apparatus of claim 1 wherein the modulator and the polarizer are separated by at least one lens element in the lens along the imaging path.

3. The apparatus of claim 1 further comprising an image sensor, said image sensor being operably configured to separately record said first and second images.

4. The apparatus of claim 3 wherein said modulator is disposed between the lens and said image sensor.

5. The apparatus of claim 1 wherein said polarizer comprises a polarizing coating applied to a surface of a lens element disposed proximate to said aperture plane.

6. The apparatus of claim 1 wherein said first and second portions of said polarizer are operable to vary in extent to cause said first and second perspective viewpoints to change location while forming said first and second images, said change in perspective viewpoint location providing a corresponding change in said representation of said three dimensional spatial attributes.

7. The apparatus of claim 1 further comprising an actuator coupled to said polarizer, said actuator being operably configured to cause an orientation of said polarizer to be rotated by 90 degrees to facilitate selectively configuring the apparatus to generate images in one of a landscape orientation and a portrait orientation.

8. The apparatus of claim 1 further comprising a first variable stop disposed in said first portion of the single imaging path proximate said polarizer and a second variable stop disposed in said second portion of the single imaging path proximate said polarizer.

9. The apparatus of claim 1 wherein the lens includes a lens group comprising one of a zoom lens group, a telephoto lens group, and a prime lens group.

10. A method for generating three-dimensional image information using a lens having a single imaging path and an associated field of view, the method comprising:
directing light captured within the field of view of the lens to an aperture plane of the lens;
receiving said captured light through a polarizer located proximate said aperture plane, said polarizer including a first portion disposed to transmit light having a first polarization state through a first portion of the single imaging path and a second portion disposed to transmit light having a second polarization state through a second portion of the single imaging path, said first and second portions of said single imaging path providing respective first and second perspective viewpoints within the field of view of the lens, wherein receiving said captured light comprises receiving light having a first polarization orientation through said first portion of said polarizer and receiving light having a second polarization orientation through said second portion of said polarizer, said first and second polarization orientations comprise any one of: respective linear polarization orientations that are orthogonal, respective left-handed and right-handed elliptical polarization orientations, and respective left-handed and right-handed circular polarization orientations, and
controlling a modulator disposed in the single imaging path to selectively change a polarization state of light passing through the modulator to alternate between forming a first image through said first portion of said single imaging path and forming a second image through said second portion of said single imaging path, said first image representing objects within the field of view from said first perspective viewpoint and said second image representing said objects from said second perspective viewpoint, said first and second images together being operable to represent three dimensional spatial attributes of said objects, wherein said modulator is disposed in the single imaging path before said polarizer, and wherein controlling said polarization state of said modulator comprises, selecting one of said first and second polarization states for transmission, and alternating between: transmitting the selected polarization state; and causing said selected polarization state to undergo a change between said first polarization orientation and said second polarization orientation.

11. The method of claim 10 wherein the step of controlling a modulator controls a modulator that is separated from the polarizer by at least one lens element along the imaging path.

12. The method of claim 10 wherein receiving said captured light at said polarizer comprises receiving the captured light at a polarizing coating applied to a surface of a lens element disposed proximate to said aperture plane.

13. The method of claim 10 further comprising varying an extent of said first and second portions of the imaging path to cause said first and second perspective viewpoints to change location while forming said first and second images, said change in perspective viewpoint location providing a corresponding change in said representation of said three dimensional spatial attributes.

14. The method of claim 10 further comprising selectively rotating said polarizer by 90 degrees to generate images in one of a landscape orientation and a portrait orientation.

15. The method of claim 10, wherein receiving said captured light through said polarizer comprises receiving captured light associated with said first portion of the single imaging path through a first variable stop and receiving captured light associated with said second portion of the single imaging path through a second variable stop.

16. The method of claim 10 further comprising separately recording said first and second images using an image sensor.

* * * * *